United States Patent
Ruiz González

(10) Patent No.: US 11,372,117 B2
(45) Date of Patent: Jun. 28, 2022

(54) DEVICE FOR ESTIMATING THE HALF-VALUE LAYER OR THE QUARTER-VALUE LAYER OF ROTATING X-RAY SOURCES USED IN COMPUTED TOMOGRAPHY

(71) Applicant: THE BOARD OF REGENTS OF THE UNIVERSITY OF TEXAS SYSTEM, Austin, TX (US)

(72) Inventor: Néstor A. Ruiz González, San Antonio, TX (US)

(73) Assignee: Board of Regents, The University of Texas Systen, Austin, TX (US)

( * ) Notice: Subject to any disclaimer, the term of this patent is extended or adjusted under 35 U.S.C. 154(b) by 18 days.

(21) Appl. No.: 17/045,632

(22) PCT Filed: Apr. 5, 2019

(86) PCT No.: PCT/US2019/025966
§ 371 (c)(1),
(2) Date: Oct. 6, 2020

(87) PCT Pub. No.: WO2019/195664
PCT Pub. Date: Oct. 10, 2019

(65) Prior Publication Data
US 2021/0157018 A1    May 27, 2021

Related U.S. Application Data

(60) Provisional application No. 62/654,016, filed on Apr. 6, 2018.

(51) Int. Cl.
G01T 1/02 (2006.01)
G01N 23/046 (2018.01)
A61B 6/03 (2006.01)

(52) U.S. Cl.
CPC .............. *G01T 1/02* (2013.01); *G01N 23/046* (2013.01); *A61B 6/032* (2013.01)

(58) Field of Classification Search
CPC ........ G01T 1/02; G01N 23/046; A61B 6/032; G01B 11/02
See application file for complete search history.

(56) References Cited

U.S. PATENT DOCUMENTS

| 6,454,460 B1 | 9/2002 | Ramanathan et al. |
| 2004/0264626 A1 | 12/2004 | Besson |
| 2007/0183590 A1 | 8/2007 | Gray |

(Continued)

FOREIGN PATENT DOCUMENTS

JP    2008194441 A  *  8/2008

OTHER PUBLICATIONS

Fukuda et al., Measurement of the half-value layer for CT systems in a single-rotation technique: Reduction of stray radiation with lead apertures, Jul. 24, 2020, Physica Medica, vol. 76, pp. 221-226. (Year: 2020).*

(Continued)

*Primary Examiner* — Christine S. Kim

(57) ABSTRACT

Certain embodiments are directed to devices useful for determination of HVL or the QVL of an x-ray source. The device includes an elongated radio-opaque cylindrical body having an incremental or continuous decrease in circumference.

23 Claims, 13 Drawing Sheets

(56) References Cited

U.S. PATENT DOCUMENTS

2008/0226038 A1 9/2008 Fox et al.
2013/0016808 A1 1/2013 Boone et al.

OTHER PUBLICATIONS

Randazzo et al., A rapid noninvasive characterization of CT x-ray sources, Jun. 10, 2015, Med. Phys., vol. 42, pp. 3960-3968. (Year: 2015).*

Okubo et al., Feasibility of the new copper pipe method for evaluating half-value layer in computed tomography: A measurement and Monte Carlo simulation study, 2019, J Appl Clin Med Phys 2019; vol. 20, pp. 186-192. (Year: 2019).*

Matsubara et al., Accuracy of measuring half- and quarter-value layers and appropriate aperture width of a convenient method using a lead-covered case in X-ray computed tomography, 2014, Journal of Applied Clinical Medical Physics, vol. 15, pp. 30-316 (Year: 2014).*

Lida et al., Measurement of Effective Energy and Entrance Surface Dose Using Fluorescent Glass Dosimeter in Interventional Radiology Procedures: Make of Half-value Layer Measurement Instrument and IVR-Phantom, Published 2010, Nihon Hoshasen Gijutsu Gakkai Zasshi., English abstract only (Year: 2010).*

McKenney et al., Real-time dosimeter employed to evaluate the half-value layer in CT, Mar. 23, 2015, Phys Med Biol. Author manuscript; pp. 1-25 (Year: 2015).*

International Preliminary Report on Patentability Issued in Corresponding PCT Patent Application No. PCT/US2019/025966, dated Oct. 6, 2020.

International Search Report and Written Opinion Issued in Corresponding PCT Patent Application No. PCT/US2019/025966, dated Jul. 9, 2019.

Tan, "Scanning and Post-Processing Parameter Optimization for CT Dimensional Metrology," Doctoral Thesis, KU Leuven, Apr. 2015, Retrieved from https://core.ac.uk/download/pdf/34626300.pdf.

* cited by examiner $$\text{Pixel Density Ratio} = \frac{(I_n - I_{BKND})}{(I_0 - I_{BKND})}$$

DEVICE FOR ESTIMATING THE HALF-VALUE LAYER OR THE QUARTER-VALUE LAYER OF ROTATING X-RAY SOURCES USED IN COMPUTED TOMOGRAPHY

RELATED APPLICATIONS

This Application is a national phase application under 35 U.S.C. § 371 of International Application No. PCT/US2019/025966, filed Apr. 5, 2019, which claims priority to U.S. Provisional Application Ser. No. 62/654,016 filed Apr. 6, 2018, which is incorporated herein by reference in its entirety.

BACKGROUND OF THE INVENTION

1. Field of the Invention

Certain embodiments are generally directed to computed tomography (CT) imaging systems and related imaging system tests or image processing methods. More particularly, the methods and devices described can be used for measuring the half-value layer (HVL) or the quarter-value layer (QVL) for CT imaging systems.

2. Description of Related Art

X-ray based imaging and other types of radiographic analysis are established diagnostic tools used in medicine. The penetrating ability of photons is one of the characteristics of x-ray radiation that make them useful for medical imaging. Photons directed at an object are either attenuated by the object, completely absorbed, or scattered. The photons penetration, and corresponding attenuation, depends on the energy of the individual photons as well as the atomic number, density, and thickness of the object that is being exposed to the radiation. The reduction in the number of photons, or attenuation, is proportional to the thickness of the attenuating material, and is typically expressed as the fraction of radiation that passes through the object. The number of photons attenuated, or removed, from the original intensity increases as the thickness of attenuating material is increased. Hence, the amount of post-attenuated photons decreases as the thickness of attenuating material is increased.

In medical x-ray imaging systems x-rays are generated using a kilo-voltage potential difference to accelerate and collide electrons on a target. These electrons will then undergo bremsstrahlung interactions with the different materials from x-ray tube, beam collimation components, or any other system components within the beam's path. The resulting useful x-ray beam spectrum will have photons of different energies, i.e., poly-energetic and consequently, different penetrability.

A common metric that is used to characterize the penetrability of an x-ray beam is called the half-value layer (HVL). The HVL is a quantification of the penetration of the x-ray beam through a material that is being examined and it is defined by the thickness of a material that reduces the transmission of the x-ray beam by 50%. The units used to express the HVL are typically millimeters or centimeters of a specific attenuating material. The HVL value is also photon energy dependent.

Photon absorbing and filtering materials can preferentially remove lower-energy x-ray photons emitted by the x-ray source and thereby filter the beam. The amount of filtration of the x-ray beam will depend on the kilo-volt-peak (kVp) potential used to produce the beam and the thickness and atomic number of filter material.

Filters used in industrial radiography to filter the x-ray beam are typically made from high atomic number materials such as copper, tin, brass, or lead. However, filters used for medical imaging radiography are normally made of aluminum. When both the applied kVp and the HVL of a spectrum are known, an x-ray spectrum is deemed well characterized. Most x-ray systems used for medical imaging have the ability to adjust the kVp, and thus it is common practice amongst medical physicists to characterize the x-ray system by measuring the HVL at three or more kVp settings.

The practice of measuring the HVL, in general, proceeds with a radiation meter (which measures the x-ray beam kinetic energy released per unit mass (kerma) in the units of mGy) that is positioned to measure a collimated (narrow) beam of x-rays from the source, and serial measurements are made. The thickness of the aluminum sheets (the attenuating material) is changed between measurements by adding additional sheets. The radiation meter is positioned 30-50 cm away from the attenuating material to minimize the contribution of scatter radiation (initiating from the attenuating material) to be detected by the radiation meter; this is commonly referred to as an "air gap". Depending on the x-ray beam spectrum/energy, the beam will be attenuated differently by the added aluminum filters. HVL values are typically from about 0.25 mm of aluminum in mammography to 7 to 15 mm aluminum in CT at high kVp settings.

The HVL can be defined/modeled, mathematically using the Lambert-Beer equation in the form of:

$$\frac{I_0}{2}(HVL) = I_0 e^{-\mu(HVL)} \qquad \text{Equation 1.0}$$

where, $$HVL = \frac{Ln(2)}{\mu} \qquad \text{Equation 2.0}$$

where $I_0$ is the photon beam intensity measured without any attenuating material in its path, and $\mu$ is the linear attenuation coefficient ($\mu$ has units of $mm^{-1}$) corresponding to the specific attenuating material and the x-ray photon's effective energy in kilo-electron-volt (keV).

The quarter-value layer (QVL) can be defined/modeled, mathematically using the Lambert-Beer equation in the form of:

$$\frac{I_0}{4}(HVL) = I_0 e^{-\mu(QVL)} \qquad \text{Equation 3.0}$$

where, $$QVL = \frac{Ln(4)}{\mu} \qquad \text{Equation 4.0}$$

For decades the HVL has been one of the standard image quality parameters in diagnostic medical x-ray imaging systems. The HVL provides an important quantitative measure of the x-ray photons penetrability. Low energy x-ray photons do not contribute to good diagnostic image quality, are mostly absorbed within the first few inches of tissue, and increase the patient's radiation dose.

Federal regulations require states in the United States to perform HVL measurements of an x-ray beam as a standard quality assurance test for transmission-type radiographic and fluoroscopic medical imaging systems. The keystone for these regulations and/or scientific standards is based on a minimum requirement HVL, as a function of kVp. If a system is not in compliance with the specified HVL standards, then corrective actions are taken and servicing of the equipment performed. HVL values may also be used as a preventive indication of equipment malfunctions or deterioration.

CT scans are medically prescribed in high volume and are one reason for the last decade's increase in the average annual effective dose to the average individual living in the U.S. The measurements of HVL can assist in providing an estimate of the x-ray beam's effective energy which is an important parameter in radiation dosimetry calculations. The x-ray beam's effective energy is also needed to find the appropriate mass-energy absorption coefficients which are then used in radiation dosimetry calculations.

However, the HVL is not routinely measured for CT scanners due to the difficulties encountered while attempting to perform the required HVL measurements. Measuring the HVL in CT scanners requires "parking" the x-ray tube (i.e., disabling the x-ray tube's rotation around the CT gantry) which can only be done by service engineers or if an option to do so is available in the CT console's menu.

SUMMARY OF THE INVENTION

The embodiments combined experimental setup and symmetrical irradiation conditions approach those of ideal broad-beam attenuation and broad-beam geometry. This allows for the direct measurement of the effective energy absorption coefficient which in turn can be used to find the effective total attenuation coefficient based on the shared effective energy value. Embodiments are capable of measuring the broad-beam geometry HVL and also estimating/predicting the narrow-beam geometry HVL via further calculations, interpolations, and linear correlations.

Certain embodiments are directed to devices useful for measuring the HVL of x-ray beams. Embodiments address problems associated with measuring HVL for CT scanners by providing a device that does not require the x-ray tube of a CT scanner to be parked during assessment of the CT scanner. Certain aspects can be adapted for use in orthovoltage and mega-volt radiation therapy systems. Various embodiments can be used to further enhance medical image quality and/or the CT patient dosimetry calculations which today are mostly based in Monte Carlo simulations. Embodiments described herein aim to solve the problems associated with HVL measurements for CT scanners and enable routine HVL measurements of an x-ray beam in an efficient and cost effective manner.

In certain aspects a device can encompass a cylindrical device having a hollow central cavity of constant diameter along the long or central axis. The device's outer surface diameter increases symmetrically, from one end to the other, perpendicular to and along the central axis, in a step-wedge fashion, creating "steps" or segments of increasing diameters and consequently of increasing attenuating material thicknesses. Each step or segment has a consistent thickness or outer diameter for a specified distance along the central axis. The outer diameter can be measured from the central axis to the outer surface or from the inner surface to the outer surface.

The device can include an external and separate supporting structure designed to hold and align the device's long axis with the x-ray tube's axis of rotation in a CT scanner. The hollow central cavity is designed to allow for the insertion of a variety of radiation probes/sensors inserts/holders (also part of the invention) and/or other commercially available radiation probes/sensors.

During the process of performing HVL measurements, the device remains centered along the x-ray tube's axis of rotation while it is incrementally advanced across the x-ray tube's axis of rotation plane, and while the x-ray tube is rotating around the axis of rotation.

Variation in the device's outer surface diameter along specified segments along the long or central axis can result in "steps" each symmetrically increasing the attenuating material thicknesses as measured perpendicular to the long or central axis from outer surface to inner surface, from 0.1, 1, 2, 3, 4, 5, 6, 7, 8, 9, 10, 11, 12, 13, 14, 15, 16, 17, 18, 19, to 20 mm, including values and ranges there between. The device's composition can be aluminum, copper, tin, resin, acrylic, or other composite materials. The device's composition, and the variation in "step" thicknesses, can be selected based on the material that would work best for a specific photon beam energy.

The device's inserts or any variations (which are claimed as part of this invention) are designed to allow for, but not limited to radiation dosimeters, photon emitting radioactive materials, or commercially available radiation probes/sensors, to be positioned inside the device's hollow central cavity. The radiation measurements, or images, resulting from the device and inserts or radiation probes/sensors combination are used to then measure the HVL.

The device's hollow central cavity along the long axis is intentionally designed to accommodate radiation probes/sensors at very close proximity from the attenuating material. Radiation transport theory predicts an increase of the magnitude of the measured radiation due to the contribution from scattered radiation.

The device's scattered radiation contribution to the measurement can be characterized and later quantified, modeled, or predicted. The scatter characterization correction can make it possible for the device to be used on HVL measurements of x-ray imaging modalities different from CT. The devices described herein should not require an inverse square law correction.

After characterizing the scatter contribution of a scanned object on a signal measured at the axis of rotation the HVL could be accurately measured in CT scanners without the need to "park" (stop) the x-ray tube. This would allow medical physicists in radiology departments/clinics to easily and effortlessly measure the HVL "on-demand" which in turn could provide early detection of any problems or deterioration related to the x-ray tube.

Certain embodiments of the present invention include, but are not limited to a device comprising of an elongated cylinder with a hollowed center along the long axis, made of a radio-opaque or metallic body, having a proximal and distal end, an inner diameter and outer diameter, the body having an initial outer diameter at the proximal end with a series of decreasing outer diameters to a minimal outer diameter at the distal end.

Certain embodiments are directed to a device for determination of the HVL of an x-ray beam comprising: a cylinder; the cylinder having a hollowed center, of a constant diameter, along the long axis; a cylinder; the cylinder having a peripheral attenuating material thickness that increases incrementally by the same amount, and of equal length, along the long axis, and ultimately creating a cylindrical "step-wedge". In certain aspects the attenuating material forms a cylinder having an outer diameter that varies, in equal incremental thickness and length, along the long axis creating a cylindrical "step-wedge." The cylindrical "step-wedge" can have approximately 5, 6, 7, 8, 9, 10, 11, 12, 13, 14, 15, 16, 17, 18, 19, to 20 "steps" or more. In particular aspects the cylindrical "step-wedge" has a hollow center. In still a further aspect the hollow center can have a constant diameter, along the long axis. In particular aspects the cylindrical "step-wedge" is fabricated from aluminum, copper, tin, resins, polymers, or carbon. The cylindrical "step-wedge" can be centered inside an encasing cylinder (which can also be part of the device) which can be filled with water, a water-like polymer, or any other tissue equivalent materials. In certain aspects the encasing cylinder can have reflective lines and/or metallic objects to assist in the process of aligning and centering it to the axis of rotation of an x-ray tube. The cylindrical "step-wedge" can be mounted or configured to be mounted to a patient table of a CT scanner to ensure and assist in centering the cylindrical "step-wedge" with the axis of rotation of an x-ray tube. In certain aspects the radiation measuring devices or other inserts are connected to a computer for data collection and analysis. The attenuation data from radiation measuring devices or other inserts can be analyzed, studied, and processed in separate CT consoles or display devices. The thickness (increase in diameter) of each step on the cylindrical "step-wedge" can increase by a constant increment and where that constant increment could be within the range of 0.1, 1, 2, 3, 4, 5, 6, 7, 8, 9, 10, 11, 12, 13, 14, 15, 16, 17, 18, 19 mm to 20 mm. The length of each step, along the long axis, on the cylindrical "step-wedge", can be constant. In certain aspects the step length is 5, 6, 7, 8, 9, 10, 11, 12, 13, 14, 15, 16, 17, 18, 19 mm to 20 mm. In particular aspects the device can be made of metal, an alloy, or a polymer. The metal can include aluminum, copper, tin, brass, lead, carbon or a metal alloy. The metal or metal alloy can be of a purity of at least or greater than 95, 98, 99, 99.9%. In certain aspects the device or the step wedge portion of the device is aluminum or an aluminum alloy. The aluminum or aluminum alloy can be of a purity of at least or greater than 95, 98, 99, 99.9% aluminum. In particular aspects the device can be configured for positioning an x-ray sensitive material/detector/sensor in the hollowed center of the device. The x-ray sensitive material can be part of a material/detector/sensor or a film. In certain aspects an x-ray sensitive film substantially covers the inner surface of the device. The material/detector/sensor or film can be reversibly position in the hollowed center of the device. In particular aspects the x-ray sensitive material is a radiochromic film, iodine, lead, or calcium, or is comprised in a thermo-luminescent dosimeter, an optically stimulated luminescence dosimeter, a solid-state detector, or other type of sensor or detector.

Other embodiments are directed to methods of using devices, apparatus, or systems described herein to measure the HVL which comprises of: obtaining radiation measurements along an axis of rotation; correcting the radiation measurements for scatter radiation contributions; estimating the HVL from the scatter-corrected radiation measurements via curve fitting to a curve following the Lambert-Beers equation.

As a result of the incident symmetrical radiation (because of the radiation source rotation and positioning of the radiation sensor within the embodiment), methods can be used to experimentally measure the energy absorption coefficient ($\mu_{en}$) in the absorbing material surrounding the detector located within the apparatus in the center of rotation because the apparatus-detector geometry achieves ideal broad-beam geometry and ideal broad-beam attenuation conditions (FIG. 5). In certain embodiments an apparatus as described herein is capable of allowing methods for experimentally measuring the mass-energy absorption coefficient of different absorbing materials and that the experimental mass-energy absorption coefficient could be used, using the NIST attenuation coefficients tables, to find the effective energy of the incident radiation beam and the expected value for the total attenuation coefficient that would result from measuring the transmission in a narrow-beam geometry. The narrow-beam geometry total attenuation coefficient could then be used to estimate the narrow-beam geometry HVL or QVL (FIG. 6).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

For decades the half-value-layer (HVL) has been the standard of image quality in diagnostic x-ray imaging. However, measuring the HVL in CT scanners requires "parking" the x-ray tube. If the scatter contribution of a solid object on a signal measured at the axis of rotation could be successfully predicted, then the HVL could be accurately measured in CT scanners without the need to "park" (stop) the x-ray tube. This would allow medical physicists in radiology departments/clinics, consulting businesses and academia worldwide to easily and effortlessly measure the HVL "on-demand" which in turn could provide early detection of any problems or deterioration related to the x-ray tube. In addition, a CT HVL Phantom can be used to further enhance the patient dosimetry calculations which today are mostly based in Monte Carlo simulations.

Embodiments are directed to devices, inserts, and methods, examples of which are shown in FIG. 1A to FIG. 4B. Variations in the methodology for using the device and inserts/probes for measuring the HVL, variations in the design of the device and/or inserts, or other variations on the device and how to use the device are disclosed herein. The methods, devices, inserts/probes, and/or data/image analysis can vary so long the objective(s) of the invention is/are attained.

Figure 2A:
FIG. 2A shows an isometric view of one embodiment of a device insert; a piece of radiochromic film is designed to fit in the hollow center of a device. The film extends thru all "steps" along the long axis.
Figure 2B:
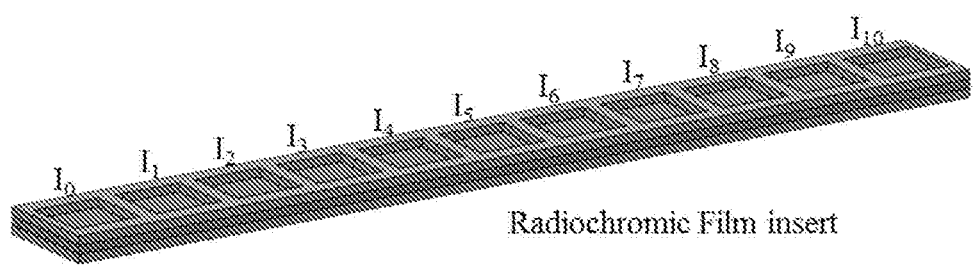
FIG. 2B shows an isometric view of one embodiment of a device insert; an insert consisting of a piece of radiochromic film placed in between a two thin frames and designed to fit in the hollow center of a device. The insert extends thru all "steps" along the long axis.
Figure 2C:
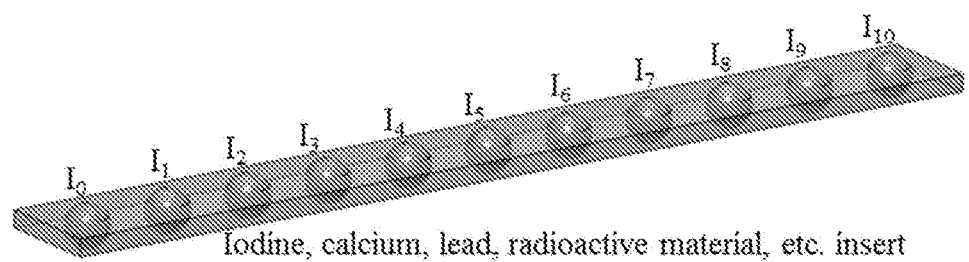
FIG. 2C shows an isometric view of one embodiment of a device insert; an insert having small samples of iodine, calcium, lead, radioactive material, or other materials/substances, placed on a thin frame and designed to fit in the hollow center of a device. The insert extends thru all "steps" along the long axis.
Figure 2D:
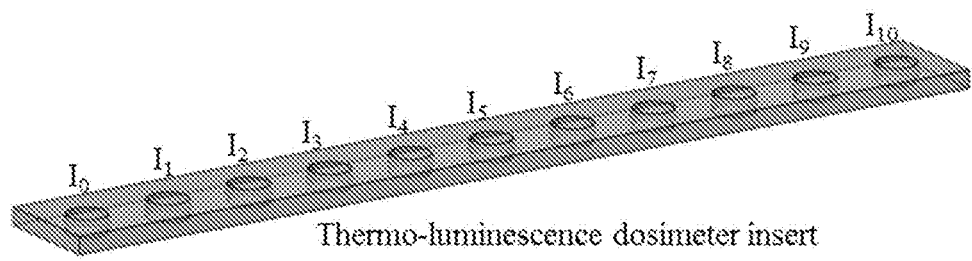
FIG. 2D shows an isometric view of one embodiment of a device insert; an insert to hold thermo-luminescence dosimeters (TLD) on a thin frame and designed to fit in the hollow center of a device. The insert extends thru all "steps" along the long axis.
Figure 2E:
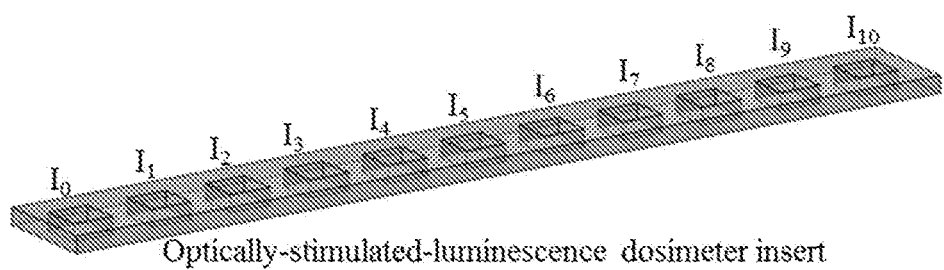
FIG. 2E shows an isometric view of one embodiment of a device insert; an insert to hold optically-stimulated-luminescence dosimeters (OSL) on a thin frame and designed to fit in the hollow of a device. The insert extends thru all "steps" along the long axis.
Figure 2F:
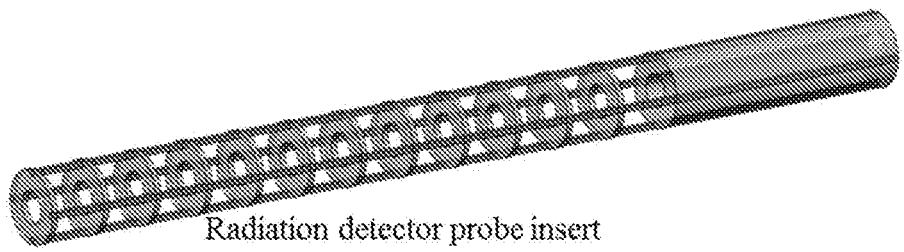
FIG. 2F shows an isometric view of one embodiment of a device insert; an insert holds a radiation probe or detector within a frame and designed to fit in the hollow center of a device. The insert extends thru all "steps" along the long axis.

Shown in FIG. 2C is an embodiment of a HVL "step-wedge" insert designed to hold radio-opaque materials such as iodine, iodine contrast, calcium, barium, lead, etc. The resulting CT scan images resulting from this insert embodiment can be analyzed to determine the attenuation thru each "step" and to then calculate the HVL. The insert can also hold small amounts of photon-emitting radioactive materials which, when inserted inside the HVL "step-wedge", can then be used to create an attenuation pattern image. The attenuation pattern image may also be used to estimate attenuation correction factors.

Figure 1A:
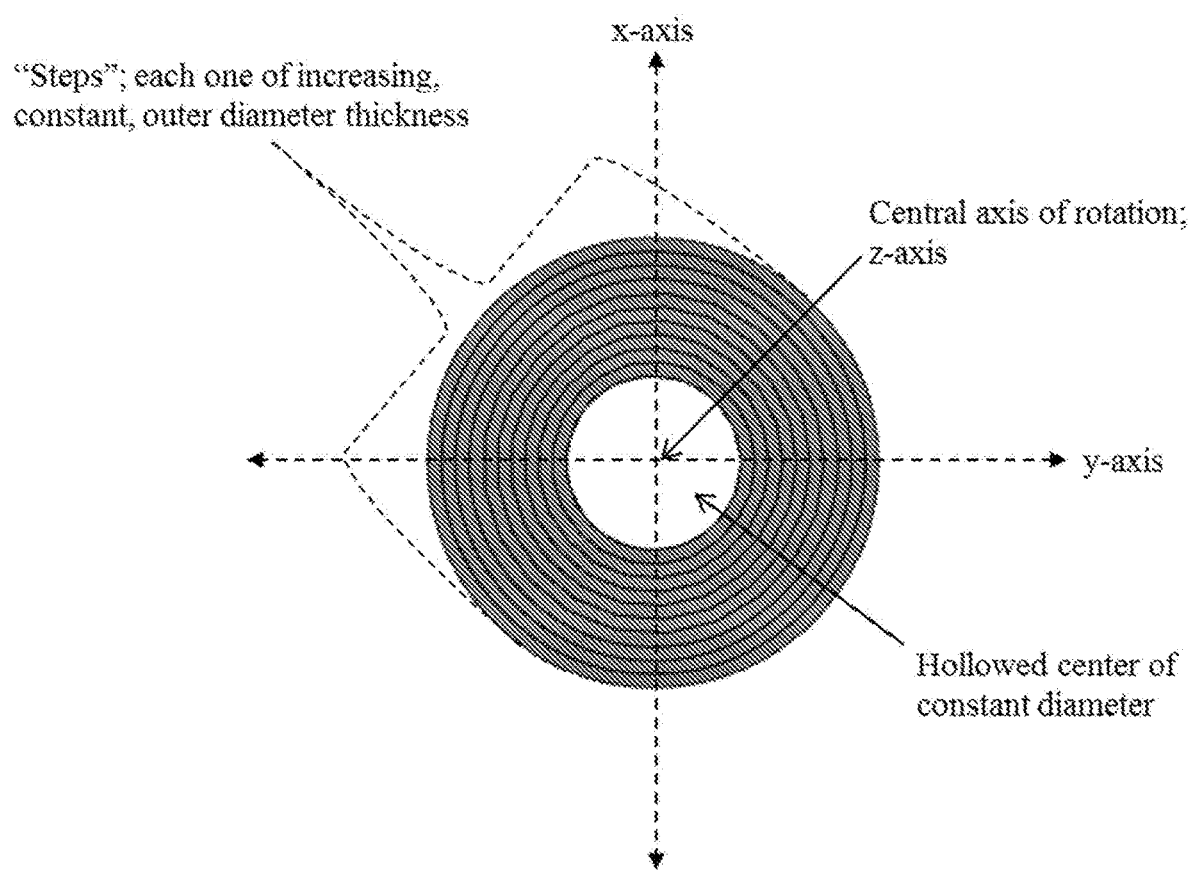
FIG. 1A shows a front view of one embodiment of a device; a HVL cylindrical "step" wedge. The hollow center is to accommodate radiation detectors, sensors, or dosimeters.
Figure 1B:
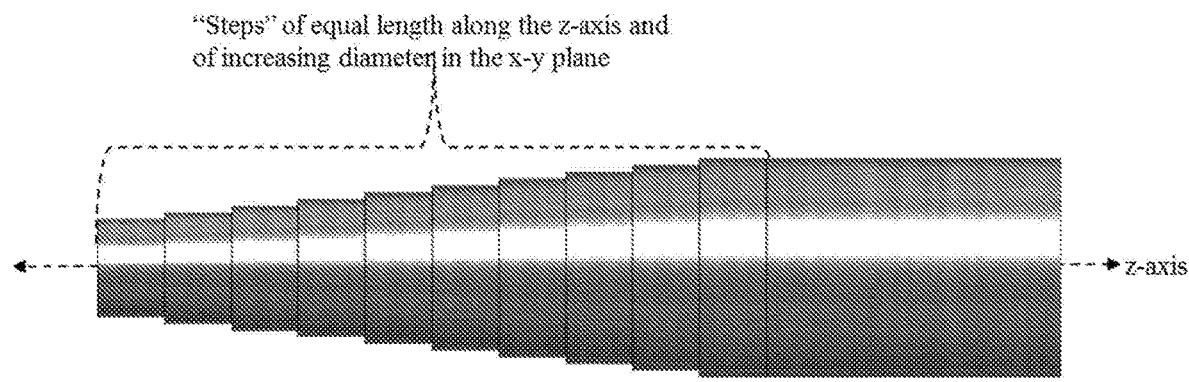
FIG. 1B shows a side/top view of one embodiment of a device; a HVL cylindrical "step" wedge. Each "step" is of equal length along the long axis and the outer diameter of the cylinder increases with every "step".
Figure 1C:
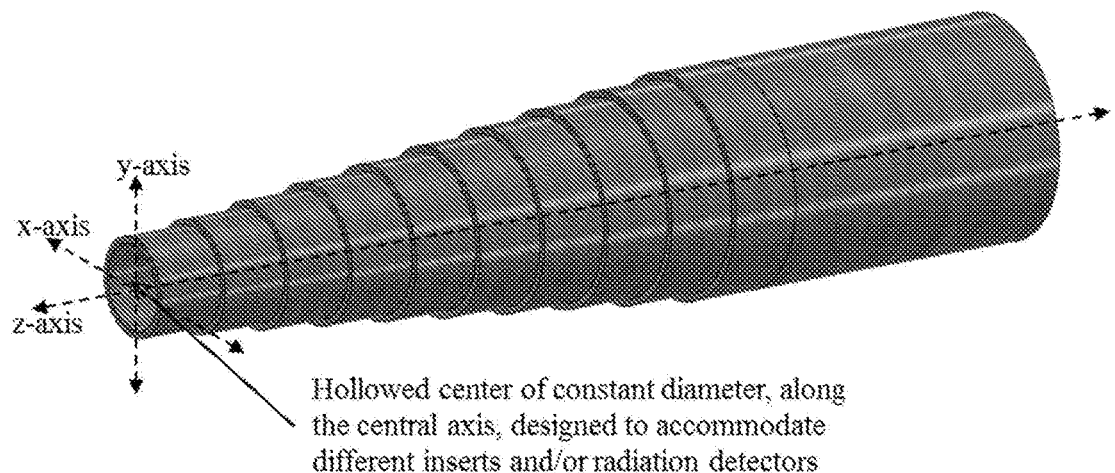
FIG. 1C shows an isometric view of one embodiment of a device; a HVL cylindrical "step" wedge. The hollow center is to accommodate radiation detectors, sensors, or dosimeters.

FIG. 1A to FIG. 1C shows an embodiment of a device to measure the HVL and can be used in CT imaging systems or other medical imaging modalities. Certain embodiments can also be referred as a HVL "step-wedge". The embodiment of the HVL "step-wedge" shown in FIG. 1A to FIG. 1C is a cylindrical device with a hollow center along the long axis (z-axis). In certain aspects the hollow center can have a constant diameter. The "steps" can be, but not necessarily, equal length along the long axis (z-axis) and of equal increasing increments in diameter (i.e., thickness) in the x-y plane from one end of the cylinder to the other.

In one embodiment the HVL "step-wedge" hollow center is designed to accommodate a radiation measuring instrument, detectors, or inserts similar, but not limited to those shown in FIG. 2A to FIG. 2F. As shown in FIG. 3A to FIG. 3C, and FIG. 4A, when the combined HVL "step-wedge" and radiation detector/insert assembly is radiated with x-ray photons that are preferentially attenuated by the different "steps" with the resulting attenuated radiation being detected/measured by the radiation detector/insert. If the x-ray tube is rotating (for example, in the x-y plane), then the long axis (z-axis) of the combined HVL "step-wedge" and radiation detector/insert assembly is centered and aligned along the x-ray tube's axis of rotation (z-axis). Notice that a portion of the radiation detector/insert can extend outside the HVL "step-wedge" to measure $I_0$ ($I_0$ is the photon beam intensity measured without any attenuating material in its path).

In one embodiment the HVL "step-wedge" is preferably made of machined aluminum, tin, copper, or any other material as needed for the intended use. The thickness and length of the "steps" can be machined to suit the photon energy and radiation source application. The embodiment of the HVL "step-wedge" shown in FIG. 1A to FIG. 1C is made of aluminum type 1100.

In one embodiment the thickness of the "steps" (i.e., outer radius minus inner radius in the x-y plane) can be machined to any thickness from approximately 0.1, 1, 2, 3, 4, 5, 6, 7, 8, 9, 10, 11, 12, 13, 14, 15, 16, 17, 18, 19, 20, 21, 22, 23, 24 mm to approximately 25 mm (including values and ranges there between) or any other thickness as needed for the intended use. The embodiment of the HVL "step-wedge" shown in FIG. 1A to FIG. 1C has "steps" (i.e., outer radius minus inner radius in the x-y plane) machined to an initial "step" thickness of 1.0 mm, then incrementing the thickness by 1.0 mm for each "step" until reaching a thickness of 10.0 mm for the last "step".

In one embodiment the length of the "steps" along the long axis (i.e. z-axis) can be machined to any length from approximately 10, 15, 20, 25, 30, 35, 40, 45 mm to approximately 50 mm (including values and ranges there between) or any other length as needed for the intended use. In one embodiment the HVL "step-wedge" shown in FIG. 1A to FIG. 1C has "steps" along the long axis (i.e., z-axis) machined to a "step" length of 10.0 mm for each "step".

In one embodiment, as shown in FIG. 3A to FIG. 3C, and FIG. 4A, the combined HVL "step-wedge" and radiation detector/insert assembly is secured to or placed on top of a patient table, centered in the axis of the x-ray tube's rotation, and then traverses, during the scan, thru the plane of the x-ray tube's rotation.

In another embodiment, as shown in FIG. 3A to FIG. 3C, and FIG. 4A, the combined HVL "step-wedge" and radiation detector/insert assembly is secured to or placed on top of a patient table, centered in the axis of the x-ray tube's rotation, and then traverses, during the scan, thru the plane while the x-ray tube remains stationary (i.e., not rotating, "parked").

Figure 3A:
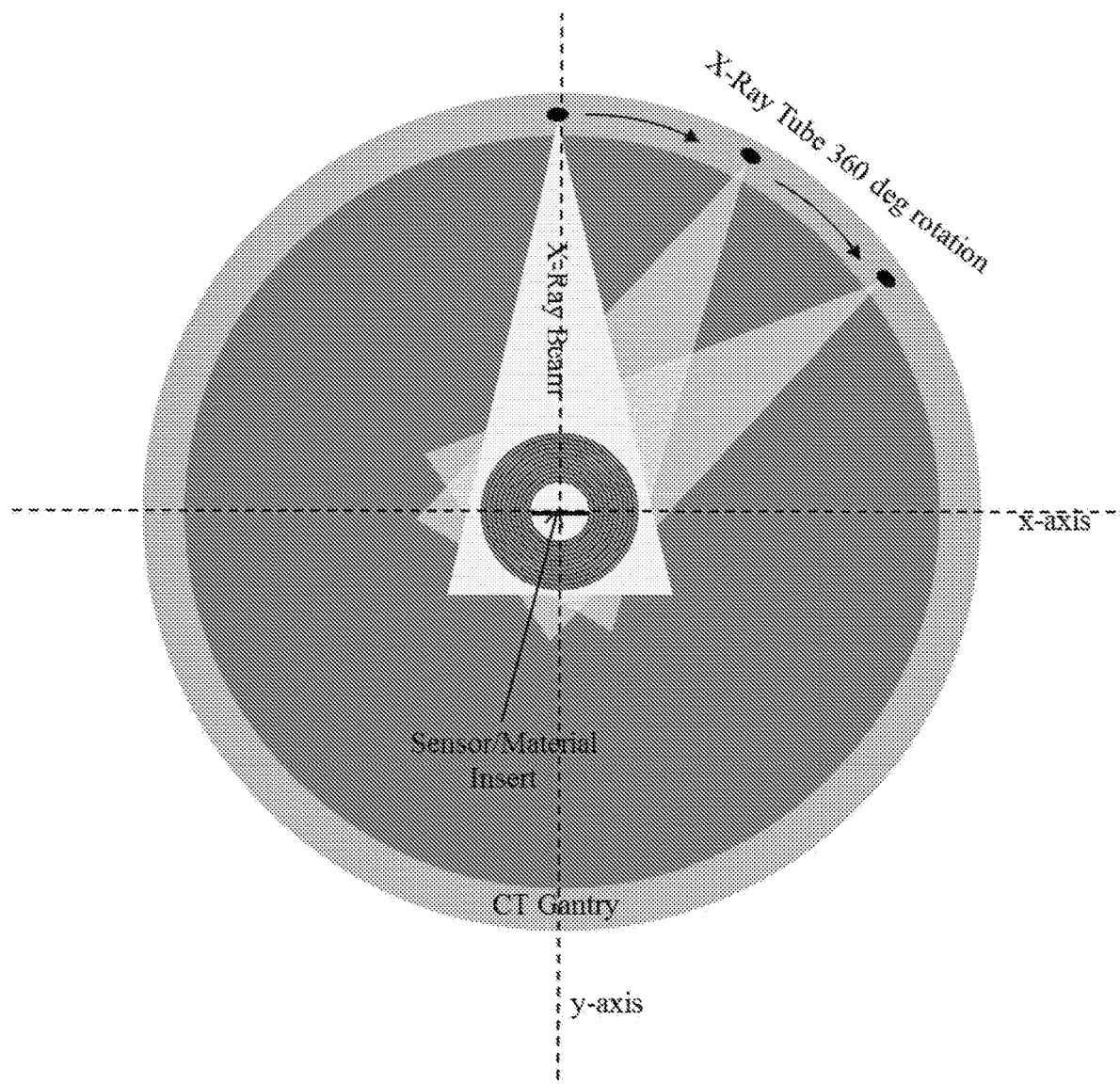
FIG. 3A shows a front view of one embodiment to perform HVL measurements where the device is centered at the axis of rotation of a CT scanner. The device is advanced thru the plane of the central axis of rotation while the x-ray beam scans the device. During the scan the x-ray tube rotates around the central axis or remains at a fixed position. A radiation detector, insert, or probe is inside the hollow center that extends along the long axis (which is also the center of rotation).
Figure 3B:
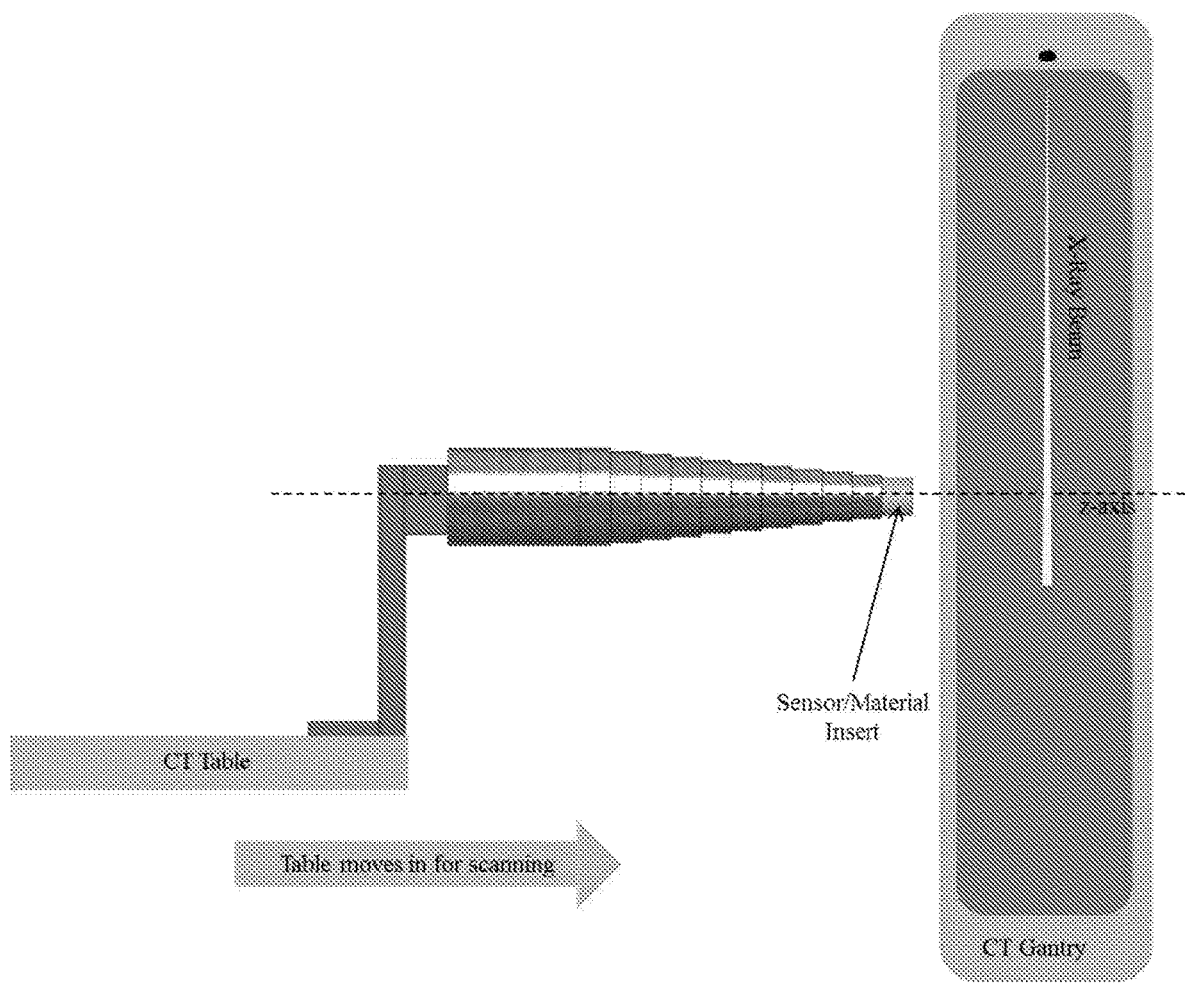
FIG. 3B shows a side view of one embodiment to perform HVL measurements where the device is centered at the axis of rotation of a CT scanner. The device is advanced thru the plane of the central axis of rotation while the x-ray beam scans the device. During the scan the x-ray tube rotates around the central axis or remains at a fixed position. A radiation detector, insert, or probe is inside the hollowed center that extends along the long axis (which is also the center of rotation). The device is held in place with a supporting structure designed to use a CT patient table to advance the device thru the plane of the central axis of rotation during the scan while avoiding radiation attenuation and scatter contributions from the table.
Figure 3C:
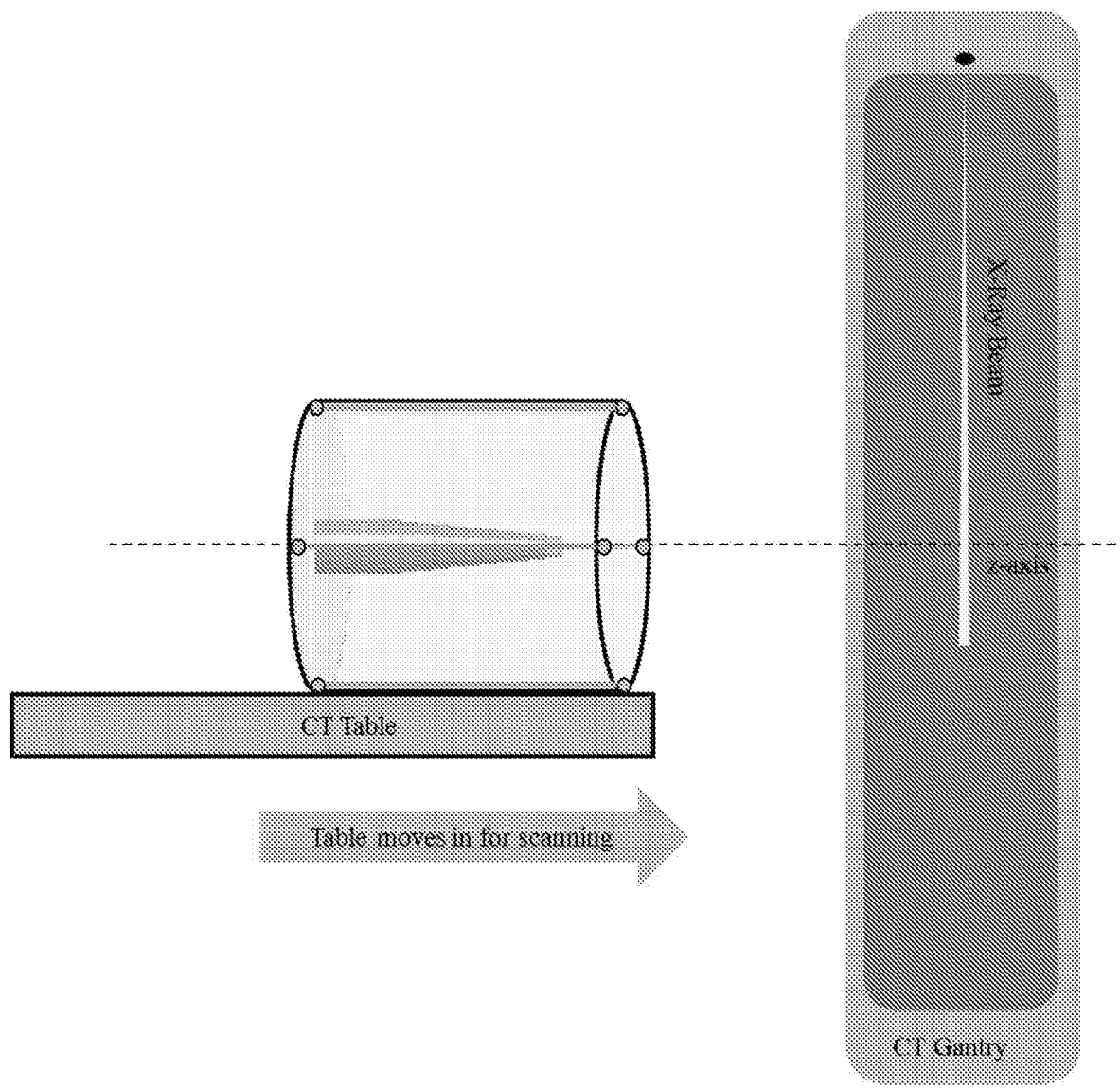
FIG. 3C shows a side view of one embodiment to perform HVL measurements where the device is centered at the axis of rotation of a CT scanner. The device is advanced thru the plane of the central axis of rotation while the x-ray beam scans the device. During the scan the x-ray tube rotates around the central axis or remains at a fixed position. A radiation detector, insert, or probe is inside the hollow center of the device that extends along the long axis (which is also the center of rotation). The device is placed inside a cylindrical casing held in place with a supporting structure designed to use a CT patient table to advance the device thru the plane of the central axis of rotation during the scan.

In another embodiment, the combined HVL "step-wedge" and radiation detector/insert assembly could be encased in a cylinder (also part of the invention) as shown in FIG. 3C which can then be filled with water, water-simulating resins, or other tissue equivalent materials. The cylinder includes reflective grooves and small metallic markers to help during the process of centering and aligning. In certain aspects the HVL is measured with the added attenuation contributions of the patient, filters, collimation, and the patient table. This in turn could result in improved input data for radiation dosimetry calculations.

It is intended that those skilled in the art understand that FIG. 3A to FIG. 3C, and FIG. 4A show either applications of this invention during scans where the x-ray tube remains stationary (i.e., not rotating, "parked") or where it rotates 360-degrees around the z-axis.

During either type of scan (rotating or stationary source) the combined HVL "step-wedge" and radiation detector/insert assembly is radiated with x-ray photons that are preferentially attenuated by the different "steps" with the resulting attenuated radiation, and $I_0$, being detected/measured by the radiation detector/insert.

Figure 4A:
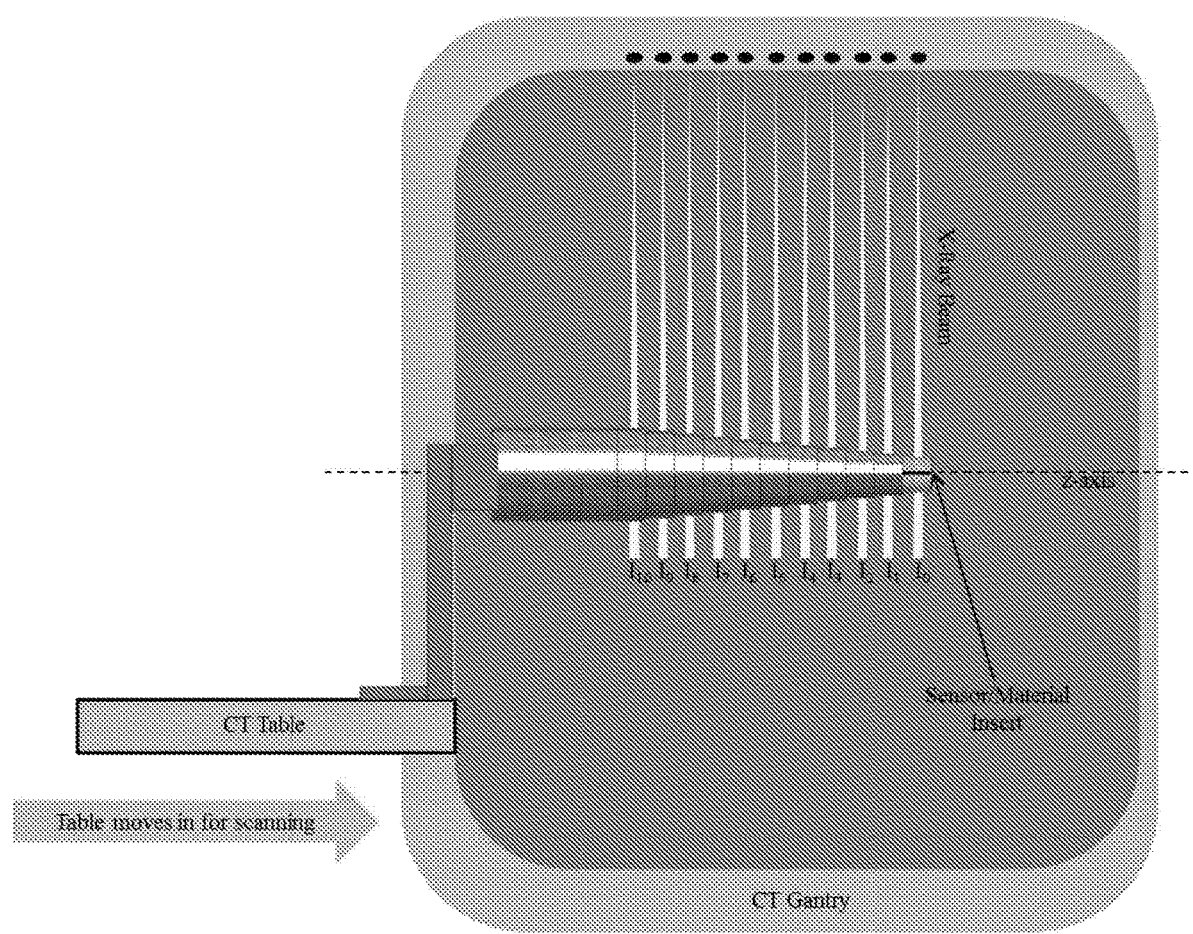
FIG. 4A shows a side view of one embodiment to perform HVL measurements where the device is centered at the axis of rotation of a CT scanner. The device is advanced thru the plane of the central axis of rotation while the x-ray beam scans the device. During the scan the x-ray beam is attenuated by the "steps" of different material thicknesses. Different radiation intensities are measured with a radiation detector, insert, or probe inside the hollow center of the device that extends along the long axis (which is also the center of rotation). A portion of the radiation detector, insert, or probe is outside the device's structure to measure the radiation intensity without any attenuating material, i.e., Jo.
Figure 4B:
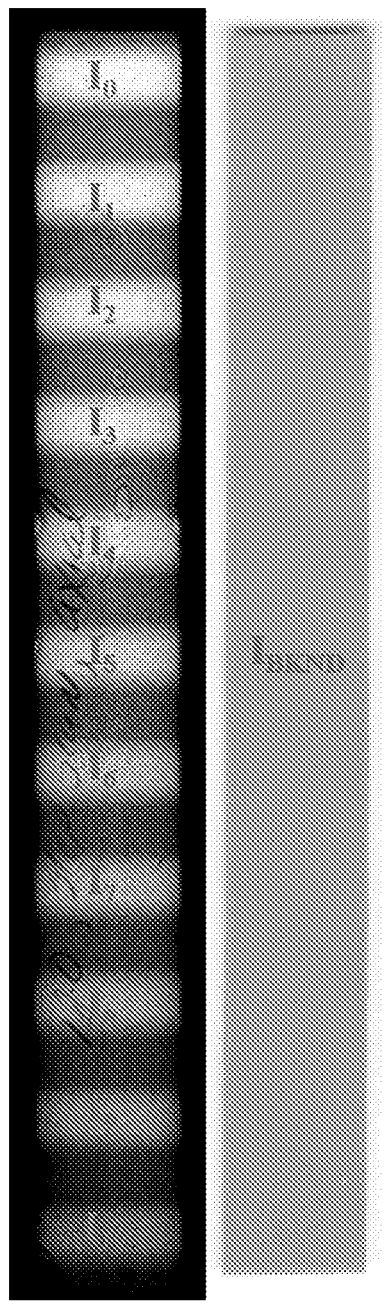
FIG. 4B shows one embodiment of an attenuation pattern after scanning the device and corresponding radiation detector, insert, or probe. An unexposed radiation sensor and a formula to calculate the pixel density ratio are also shown.
Figure 5:
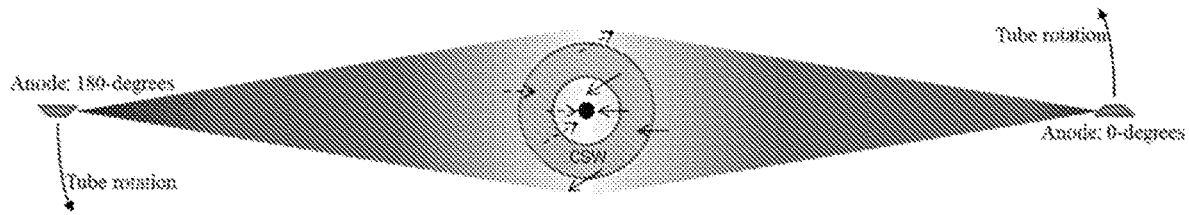
FIG. 5 illustrates that symmetrical scatter contribution within the apparatus approaches ideal broad-beam geometry/attenuation conditions. As the x-ray tube rotates, the same amount of photons lost due to scatter are replaced when the tube is in the opposite location and detected within the ion chamber's sensitive volume.
Figure 6:
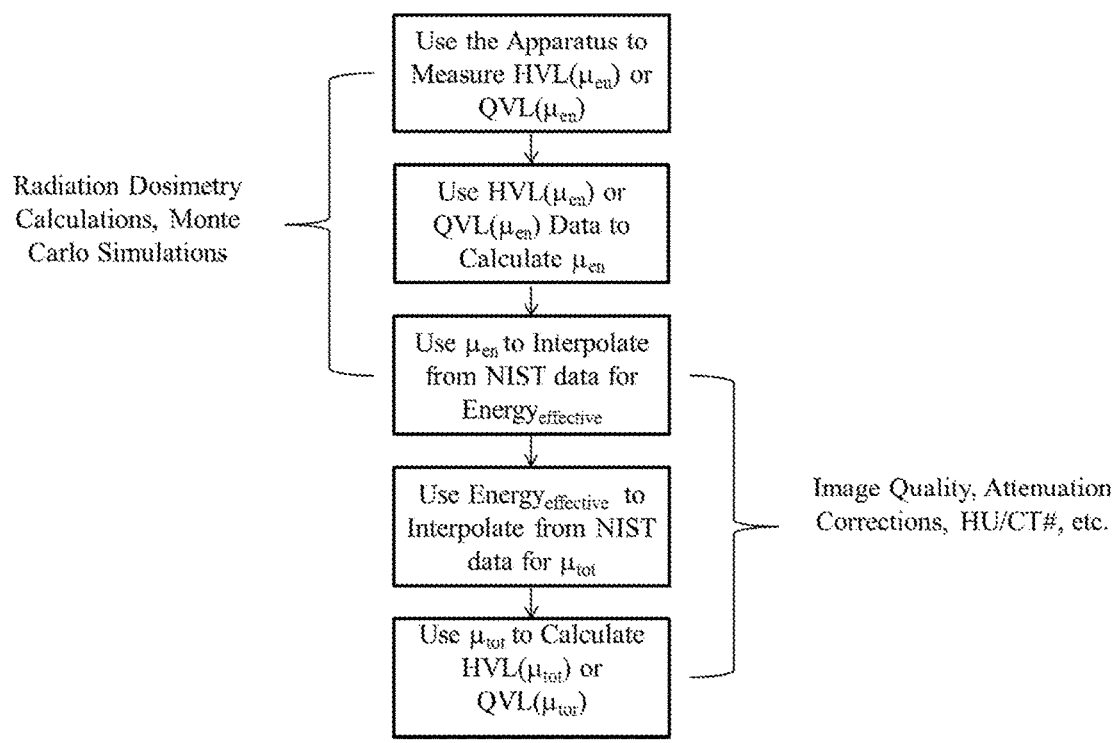
FIG. 6 is a flow chart illustrating the steps included in measurement of mass-energy absorption coefficient and/or the narrow-beam geometry HVL or QVL.

The embodiment shown in FIG. 4A is an example of the HVL "step-wedge" and radiation detector/insert assembly being exposed to x-ray photons as the table moves it thru the beam. An example of the resulting attenuation pattern is shown in FIG. 4B. The attenuation pattern could be measured with passive radiation dosimeters (such as film, TLDs, OSLs), a radiation detector/probe capable of real-time rapid data acquisition, or via analysis of the resulting CT scan images. The measured attenuation data, or an attenuation ratio, can be fitted to an equation similar to Equation 1.0 and then proceed to estimate the HVL using Equation 2.0.

In certain aspects the HVL "step-wedge" shown in FIG. 1A to FIG. 1C the radiation dosimeters, inserts, or radiation detector/probe will be in close proximity (in the order of millimeters) to the inner circumference that defines the hollowed cavity along the long axis. The close proximity of the radiation dosimeters, inserts, or radiation detector/probe to the attenuating material will introduce an increased measured attenuation due to scatter "contamination" from the attenuating material. The traditional methodology to measure the HVL uses an "air-gap" of several centimeters to avoid the increased attenuation measured due to scatter "contamination" originating from the attenuating material. It is contemplated that the HVL "step-wedge" can also be used to estimate/characterize the magnitude of the scatter "contamination" to the measured attenuation. The attenuation measured can then be corrected, predicted, or modeled to account for the scatter "contamination".

The embodiment of the HVL "step-wedge" shown in FIG. 1A to FIG. 1C results in an easy to handle and easy to use device which allows for many repeated HVL measurements and consequently more precise results. The most common application of this device, system, and/or related methods will use axial CT scans with narrow beams centered over the length of each "step" and with long rotation times over each "step". The HVL "step-wedge" and radiation detector/insert assembly remains static, centered with the axis of the x-ray tube's rotation (z-axis).

It is intended that those skilled in the art understand that the maximum attenuating material thickness of the "steps" in the embodiment shown in FIG. 1A to FIG. 1C should be, based on knowledge of the photon energy and the attenuating material, greater than the expected HVL. For example, in diagnostic radiology this maximum thickness could be at least 15-20 mm of aluminum.

The embodiment of the HVL "step-wedge" and radiation detector/insert assembly described herein should not require cupping (parallax) effect or, when properly centered and aligned along the x-ray tube axis of rotation, any inverse square corrections. However, a scatter correction/prediction/model may be required and/or recommended. The HVL can also be defined in terms of a factor applied to the HVL as measured using the traditional HVL measurement technique.

Example

Figure 7:
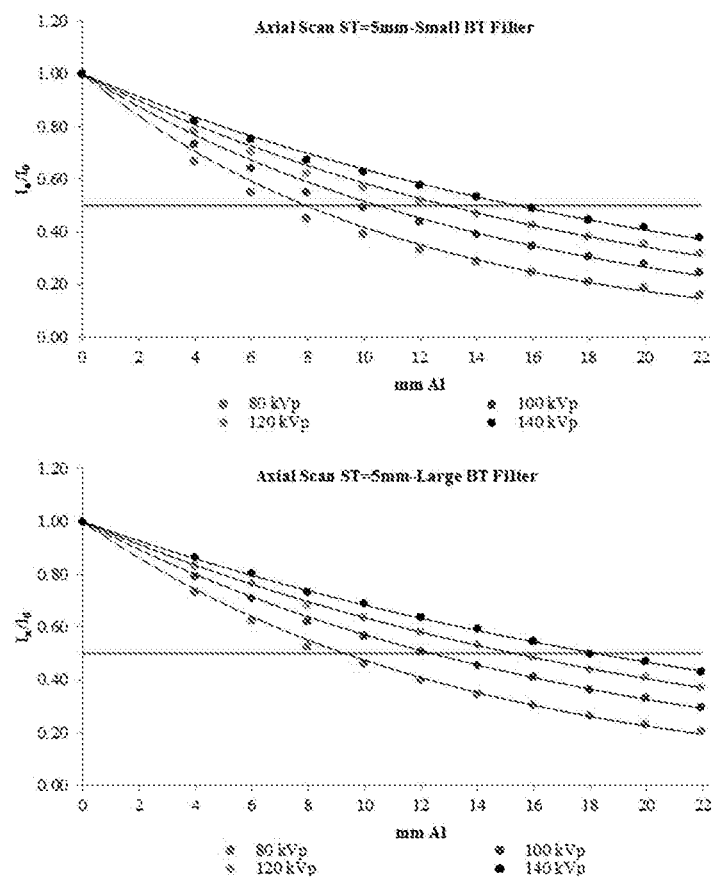
FIG. 7 shows broad-beam geometry transmission/attenuation curves (small and large BT, ST=5 mm) obtained with using one embodiment of the device described herein.
Figure 8:
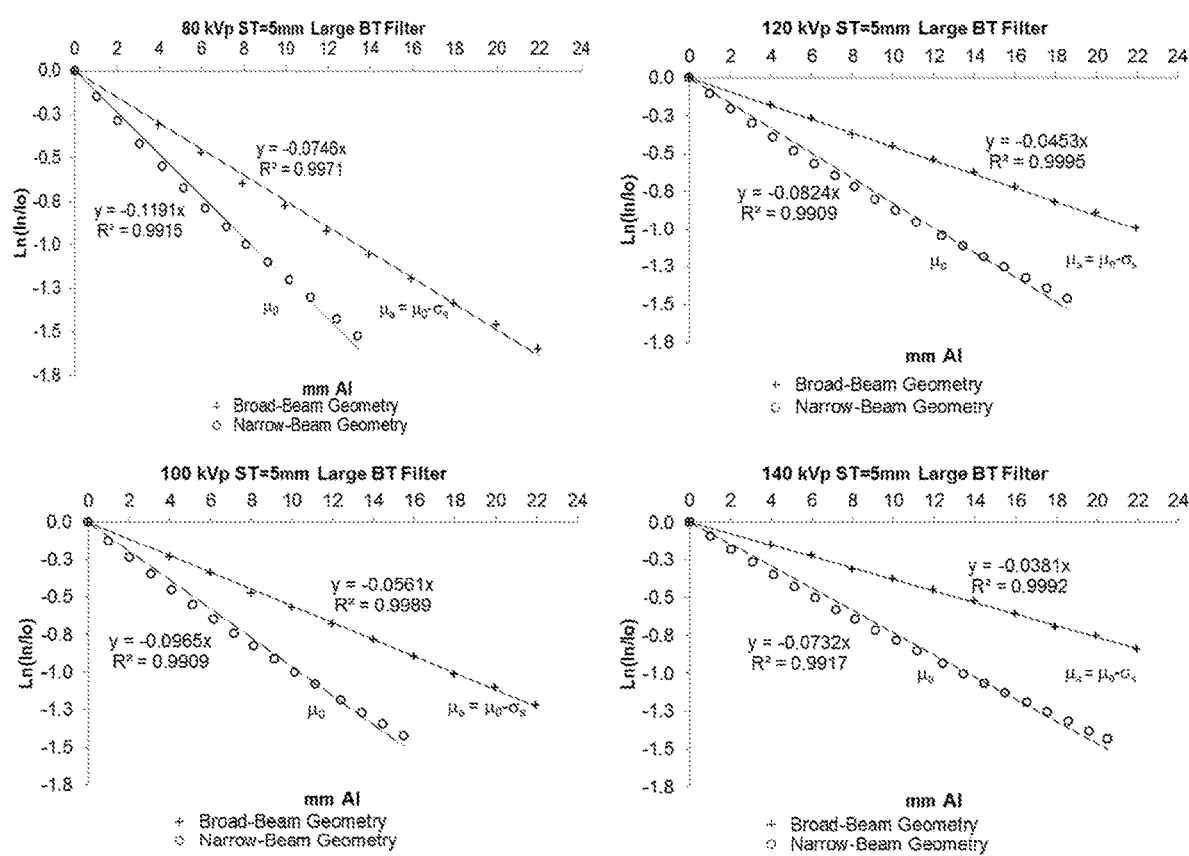
FIG. 8 shows graphical results showing (large bow-tie filter only), as theorized by Evans, the experimental setup may approach ideal broad-beam geometry and ideal broad-beam attenuation conditions.
Figure 9:
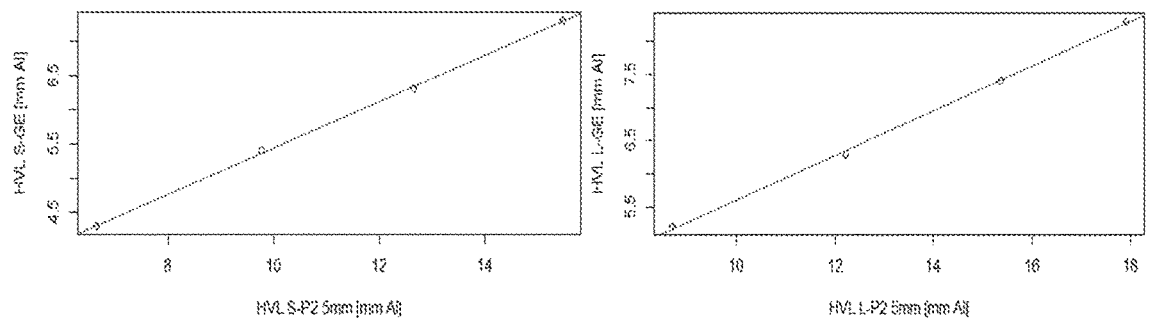
FIG. 9 shows linear regression model for the narrow-beam geometry HVL quoted by the manufacturer as a function of the broad-beam geometry HVL measured using an embodiment described herein.
Figure 10:
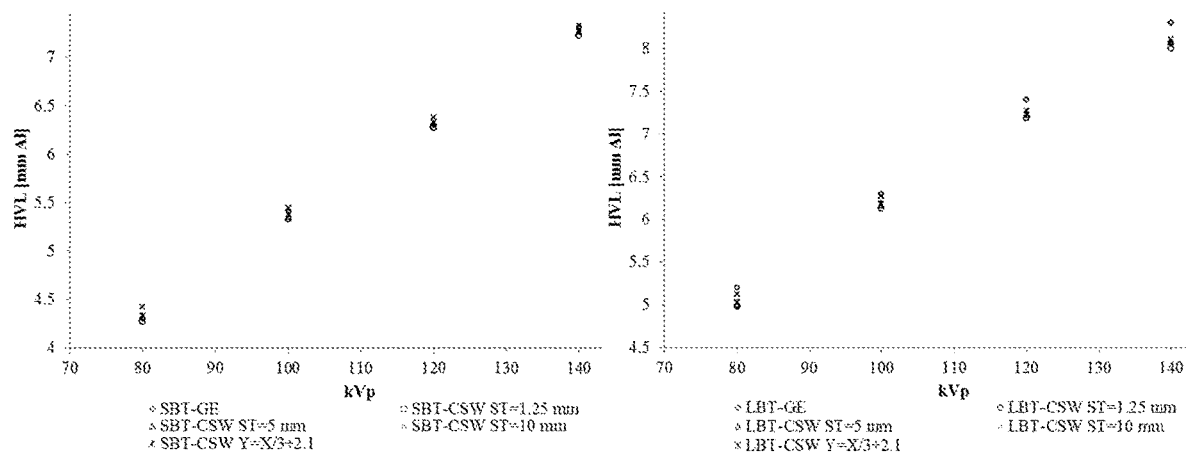
FIG. 10 shows narrow-beam geometry HVL quoted by the manufacturer and straight-line linear regression models (ST=1.25, 5, 10 mm, simplified fit), as a function of tube potential (small and large BT filters).
Figure 11:
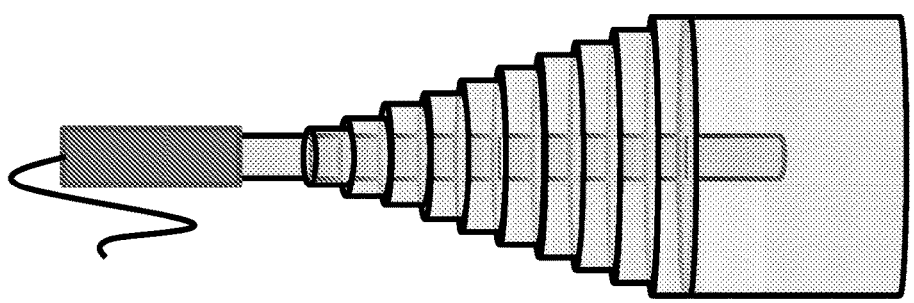
FIG. 11 shows the use of a pencil-type ion chamber for expedient, real-time, measurements and eliminates the need for post-processing required for other type of detectors like radiochromic film, TLDs, or OSLs.

A device prototype was fabricated as per the embodiment of the HVL "step-wedge" and radiation detector/insert assembly shown in FIG. 1A to FIG. 1C and FIG. 3B. The prototype was exposed to rotating x-ray beams in a setup similar to FIG. 3B and FIG. 4A and, using a pencil-type ion chamber, an attenuation curves similar to those shown in FIG. 7 were obtained.

The measured attenuation data, or an attenuation ratio, was fitted to an equation similar to Equation 1.0 to estimate the HVL using Equation 2.0.

The HVL "step-wedge" and radiation detector/insert assembly together with knowledge of the scatter contribution of a solid object on the attenuation measured at the axis of rotation, can be used to accurately measure the HVL in CT scanners without the need to "park" (stop) the x-ray tube.

In certain embodiments, an apparatus was designed to measure the HVL of an incident x-ray beam from a rotating CT x-ray tube. The design allows for using a pencil-type ion chamber, centered within the apparatus to perform the necessary measurements. Measurements were performed using an axial scan protocol with the x-ray tube set to complete one rotation per second while acquiring one image per slice. The scan was repeated for multiple tube potentials, bow-tie filters and slice thicknesses. The results were compared to HVL values quoted for the manufacturer and HVL values obtained using the localizer or scout scan.

The HVL measurements performed with the apparatus were fitted using a straight-line linear model to the HVL values quoted by the manufacturer and to the HVL values obtained using the scout scan resulting in regression coefficients of determination $r^2 \geq 0.9985$, regression p-values $\leq 0.0007$, and percent differences $\leq 4.22\%$. The Pearson product-moment correlation coefficients were; $r \geq 0.99$ (p-values $\leq 0.0007$, 95% CI 0.96 to 0.99).

Attenuation curves, and corresponding HVL measurements, can be successfully obtained using the apparatus designed. A simplified straight-line equation can be used to correlate the HVL measured using the apparatus in broad-beam geometry to the expected narrow-beam geometry HVL.

Materials: GE LightSpeed® RT 16 Slice CT scanner, RaySafe X2 (X2 Base Unit and X2 CT Sensor), and Aluminum plates (1100 alloy).

HVL Scan protocol: Axial scan; ST=1.25, 5.0, 10 mm; 1 sec tube rotation; 1 image/slice; 80, 100, 120, 140 kVp; 350 mA; and Large, Small BT filters.

Certain embodiments provide a new paradigm for estimating radiation dose and quality control. Devices and methods described herein provide for (i) a CT HVL and dosimetry protocol for after CT installation and acceptance testing, (ii) data for Monte Carlo simulations, other dosimetry models, (iii) optimization of scan protocols to further reduce dose to the patient while still maintaining good clinical image quality. In certain aspects devices described herein can be portable and easy to use. Such devices can obtain beam attenuation measurements for estimating the HVL and can be used with instrumentation already available. Certain aspects allows for measurements with the x-ray tube rotating. The HVL correlates to the manufacturer's HVL values by <5% difference.

TABLE 1

Broad-beam geometry HVL (small and large BT filters, ST = 5 mm) estimated from the broad-beam geometry transmission curves obtained with the MuCT ™ device, a cylindrical step-wedge (CSW), and using Log-linear (LL) and Lambert W (LW) interpolation.

| kVp | SBT-BBG (LL) [mm Al] | LBT-BBG (LL) [mm Al] | SBT-BBG (LW) [mm Al] | LBT-BBG (LW) [mm Al] |
|---|---|---|---|---|
| 80 | 6.93 | 8.71 | 6.82 | 8.80 |
| 100 | 9.76 | 12.21 | 9.67 | 12.21 |
| 120 | 12.65 | 15.37 | 12.65 | 15.42 |
| 140 | 15.47 | 17.91 | 15.53 | 18.66 |

TABLE 2

Effective energy-absorption coefficient estimated from Table 1 values (MUen = Ln 2/HVL).

| kVp | SBT-MUen (LL) [1/mm] | LBT-MUen (LL) [1/mm] | SBT-MUen (LW) [1/mm] | LBT-MUen (LW) [1/mm] |
|---|---|---|---|---|
| 80 | 0.1000 | 0.0796 | 0.1016 | 0.0788 |
| 100 | 0.0710 | 0.0568 | 0.0717 | 0.0568 |
| 120 | 0.0548 | 0.0451 | 0.0548 | 0.0450 |
| 140 | 0.0448 | 0.0387 | 0.0446 | 0.0371 |

TABLE 3

Effective energy estimated interpolating Table 2 values using the NIST X-Ray Mass Attenuation Coefficient and Mass Energy-Absorption Coefficient tables for aluminum.

| kVp | SBT-Eeff (LL) [keV] | LBT-Eeff (LL) [keV] | SBT-Eeff (LW) [keV] | LBT-Eeff (LW) [keV] |
|---|---|---|---|---|
| 80 | 39.28 | 42.24 | 39.00 | 42.35 |
| 100 | 44.00 | 47.47 | 43.92 | 47.47 |
| 120 | 48.12 | 51.44 | 48.11 | 51.53 |
| 140 | 51.87 | 54.49 | 52.01 | 55.18 |

TABLE 4

Effective total attenuation coefficient estimated interpolating Table 3 values using the NIST X-Ray Mass Attenuation Coefficient and Mass Energy-Absorption Coefficient tables for aluminum.

| kVp | SBT-MUtot (LL) [1/mm] | LBT-MUtot (LL) [1/mm] | SBT-MUtot (LW) [1/mm] | LBT-MUtot (LW) [1/mm] |
|---|---|---|---|---|
| 80 | 0.1568 | 0.1341 | 0.1586 | 0.1330 |
| 100 | 0.1242 | 0.1078 | 0.1249 | 0.1078 |
| 120 | 0.1055 | 0.0942 | 0.1057 | 0.0939 |
| 140 | 0.0938 | 0.0864 | 0.0935 | 0.0845 |

TABLE 5

Narrow-beam geometry HVL (small and large BT filters, ST = 5 mm) estimated using Table 4 values (HVL = Ln 2/MUtot). The percent relative differences comparing the results with the HVL values quoted by the manufacturer are shown in parenthesis.

| kVp | SBT Mfr. [mm Al] | LBT Mfr. [mm Al] | SBT (LL) [mm Al] | SBT (LL) % | LBT (LL) [mm Al] | LBT (LL) % | SBT (LW) [mm Al] | SBT (LW) % | LBT (LW) [mm Al] | LBT (LW) % |
|---|---|---|---|---|---|---|---|---|---|---|
| 80 | 4.3 | 5.2 | 4.42 | (2.85) | 5.17 | (0.48) | 4.37 | (1.65) | 5.21 | (0.22) |
| 100 | 5.4 | 6.3 | 5.58 | (3.33) | 6.43 | (2.02) | 5.55 | (2.69) | 6.43 | (2.01) |
| 120 | 6.3 | 7.4 | 6.57 | (4.23) | 7.36 | (0.49) | 6.56 | (4.20) | 7.38 | (0.27) |
| 140 | 7.3 | 8.3 | 7.39 | (1.28) | 8.02 | (3.35) | 7.41 | (1.50) | 8.20 | (1.16) |

TABLE 6

Narrow-beam geometry HVL as quoted by the manufacturer and broad-beam geometry HVL measured using the CSW with the small and large BT filters. The small relative difference of the average of all slice thicknesses to that of ST = 5 mm suggests that one can just use ST = 5 mm for expedient measurements.

| kVp | Small BT-GE ST = ? [mm Al] | Small BT-CSW ST = 1.25 mm [mm Al] | Small BT-CSW ST = 5 mm [mm Al] | Small BT-CSW ST = 10 mm [mm Al] | Average of All ST [mm Al] | Relative Difference (%) of Average to ST = 5 mm |
|---|---|---|---|---|---|---|
| 80 | 4.3 | 6.50 | 6.64 | 6.96 | 6.70 | 0.90 |
| 100 | 5.4 | 9.69 | 9.76 | 10.03 | 9.83 | 0.71 |
| 120 | 6.3 | 12.52 | 12.65 | 12.84 | 12.67 | 0.16 |
| 140 | 7.3 | 15.35 | 15.47 | 15.66 | 15.50 | 0.19 |

| kVp | Large BT-GE ST = ? [mm Al] | Large BT-CSW ST = 1.25 mm [mm Al] | Large BT-CSW ST = 5 mm [mm Al] | Large BT-CSW ST = 10 mm [mm Al] | Average of All ST [mm Al] | Relative Difference (%) of Average to ST = 5 mm |
|---|---|---|---|---|---|---|
| 80 | 5.2 | 8.64 | 8.71 | 9.06 | 8.81 | 1.14 |
| 100 | 6.3 | 12.10 | 12.21 | 12.51 | 12.27 | 0.49 |
| 120 | 7.4 | 15.27 | 15.37 | 15.52 | 15.39 | 0.13 |
| 140 | 8.3 | 17.70 | 17.91 | 18.02 | 17.88 | 0.17 |

TABLE 7

Summary of the results for the straight-line linear regression models with the corresponding minimum and maximum relative difference. The small BT and large BT filters are indicated by "S" and "L", respectively.

| X | Y | Slope | Intercept | Relative Difference Min (%) | Relative Difference Max (%) |
|---|---|---|---|---|---|
| S-CSW ST = 1.25 mm | S-GE | 0.337067 | 2.111699 | 0.08 | 0.51 |
| S-CSW ST = 5 mm | S-GE | 0.337097 | 2.072163 | 0.17 | 0.68 |
| S-CSW ST = 10 mm | S-GE | 0.342340 | 1.931753 | 0.09 | 0.62 |
| L-CSW ST = 1.25 mm | L-GE | 0.341893 | 2.209314 | 0.40 | 0.72 |
| L-CSW ST = 5 mm | L-GE | 0.337673 | 2.225142 | 0.18 | 0.77 |
| L-CSW ST = 10 mm | L-GE | 0.347425 | 2.012409 | 0.08 | 0.96 |
| S CSW (simplified fit) | S GE | ⅓ | 2.1 | 0.27 | 2.76 |
| L CSW (simplified fit) | LGE | ⅓ | 2.1 | 0.45 | 4.22 |

The invention claimed is:

1. A device for half-value layer measurements and quarter-value layer measurements comprising:
a hollow cylinder having a proximal and distal end, and constant inner diameter and a variable outer diameter along a central axis, the hollow cylinder having an initial outer diameter at the proximal end with a series of segments having decreasing outer diameters to a minimal outer diameter at the distal end.

2. The device of claim 1, wherein the constant inner diameter is 5 mm to 20 mm.

3. The device of claim 1, wherein the constant inner diameter is 13 mm.

4. The device of claim 1 wherein the outer diameter is between 13.2 mm and 50 mm.

5. The device of claim 1, wherein the minimal outer diameter is 13.2 mm.

6. The device of claim 1, wherein the initial outer diameter is 50 mm.

7. The device of claim 1, wherein the outer diameter increases from the distal end to the proximal end by 0.1 to 3 millimeter in 10 mm to 50 mm segments or steps.

8. The device of claim 1, wherein the outer diameter of a segment increases by either 1 mm or 2 mm per segment from the distal end to the proximal end.

9. The device of claim 1, wherein each segment is 10 mm in length as measured along the central axis.

10. The device of claim 1, comprising 5 to 20 segments having an incremental increase in the outer diameter from the distal end to the proximal end.

11. The device of claim 1, wherein the device is metal, a metal alloy, solid-state semiconductor, or a polymer material.

12. The device of claim 11, wherein a percentage aluminum in the aluminum or aluminum alloy is 99% aluminum or greater.

13. The device of claim 1, wherein the device is aluminum, copper, tin, brass, lead, or a metal alloy.

14. The device of claim 1, wherein the device is aluminum or an aluminum alloy.

15. The device of claim 1, wherein the device body has an alignment point, or alignment line, or both an alignment point and an alignment line.

16. The device of claim 1, further comprising a cylindrical casing.

17. The device of claim 16, wherein the cylindrical casing is hollow or the cylindrical casing is filled with a liquid or a solid.

18. The device of claim 17, wherein the liquid is water.

19. The device of claim 17, wherein the solid is a polymer, polymer gel, tissue equivalent material, or material simulating water.

20. The device of claim 1, further comprising an x-ray radio-opaque material, or radiation detector positioned in the hollow cylinder.

21. The device of claim 20 wherein the radiation detector is an ion chamber, solid-state semiconductors, thermo-luminescence dosimeters, optically-stimulated dosimeters, or radiochromic film.

22. The device of claim 21, wherein the radiochromic film substantially covers an inner surface of the hollow cylinder.

23. An apparatus for half value layer measurements of x-ray sources comprising a device of claim 1 and a radiation detector or radio-opaque material operatively positioned within the device.

* * * * *